(12) United States Patent
Banerjee et al.

(10) Patent No.: US 7,734,428 B2
(45) Date of Patent: Jun. 8, 2010

(54) METHOD OF PRODUCING THERMOELECTRIC MATERIAL

(75) Inventors: Debasish Banerjee, Ann Arbor, MI (US); Minjuan Zhang, Ann Arbor, MI (US)

(73) Assignee: Toyota Motor Engineering & Manufacturing North America, Inc., Erlanger, KY (US)

( * ) Notice: Subject to any disclaimer, the term of this patent is extended or adjusted under 35 U.S.C. 154(b) by 292 days.

(21) Appl. No.: 11/875,266

(22) Filed: Oct. 19, 2007

(65) Prior Publication Data

US 2009/0105988 A1  Apr. 23, 2009

(51) Int. Cl.
*G01N 31/00* (2006.01)
(52) U.S. Cl. ............................................ 702/30
(58) Field of Classification Search .................. 702/27, 702/33, 34, 133, 136, 30, 65; 136/201, 236.1
See application file for complete search history.

(56) References Cited

U.S. PATENT DOCUMENTS

| | | | | |
|---|---|---|---|---|
| 3,073,883 | A * | 1/1963 | McHugh et al. | 136/238 |
| 4,717,788 | A * | 1/1988 | Rauch et al. | 136/237 |
| 5,886,390 | A | 3/1999 | Nishimoto et al. | |
| 6,605,772 | B2 | 8/2003 | Harman et al. | |
| 7,002,071 | B1 * | 2/2006 | Sadatomi et al. | 136/239 |
| 7,255,922 | B2 | 8/2007 | Take et al. | |
| 2006/0102224 | A1 * | 5/2006 | Chen et al. | 136/203 |
| 2006/0118158 | A1 | 6/2006 | Zhang et al. | |

FOREIGN PATENT DOCUMENTS

WO  2007/066820  * 6/2007
WOWO-PCT/JP2006/
324891  6/2007

OTHER PUBLICATIONS

Woochul Kim et al; Phonon Scattering Cross Section of Polydispersed Spherical Nanoparticles; Journal of Applied Physics; 2006; pp. 084306-1-084306-7.
Woochul Kim et al; Thermal Conductivity Reduction And Thermoelectric Figure of Merit Increase By Embedding Nanoparticles In Crystalline Semiconductors; Physical Review Letters; 2006; 045901-1-045901-4.

* cited by examiner

*Primary Examiner*—Michael P Nghiem
(74) *Attorney, Agent, or Firm*—Gifford, Krass, Sprinkle, Anderson & Citkowski, P.C.

(57) ABSTRACT

A process for determining an optimum range of compositions for a nanocomposite thermoelectric material system is provided. The process is performed for a nanocomposite thermoelectric material system having a first component and a second component made from nanoparticles. The process includes selecting a plurality of material compositions for a nanocomposite thermoelectric material system to be investigated and calculating a thermal conductivity value and calculating an electrical resistance value for each material composition selected. In addition, at least one Seebeck coefficient is determined for the material compositions selected. Then, a plurality of figure of merit values are calculated using the calculated plurality of thermal conductivity values, the calculated plurality of electrical resistivity values and the determined at least one Seebeck coefficient. After the plurality of figure of merit values are calculated, an optimum compositional range can be determined within which the largest ZT values may be exhibited.

14 Claims, 7 Drawing Sheets

METHOD OF PRODUCING THERMOELECTRIC MATERIAL

FIELD OF THE INVENTION

This invention relates to materials having thermoelectric properties and to thermoelectric devices.

BACKGROUND OF THE INVENTION

A thermoelectric device can be used to obtain electrical energy from a thermal gradient (for example, a thermoelectric generator using the Seebeck effect), or to generate a thermal gradient from electrical energy (for example, a thermoelectric refrigerator using the Peltier effect). The discussion below is directed to the Seebeck effect, but the general concepts also apply to applications of the Peltier effect.

A typical thermoelectric device is built up from several unicouples, which are typically pairs of thermally conductive p-type (P) and n-type (N) semiconductors. These unicouples are connected electrically in series and thermally in parallel. Theoretically, the maximum efficiency of the conversion of heat energy to electrical energy is given by:

$$\zeta_{max} = \frac{(T_H - T_C)}{T_H} \frac{\sqrt{1 + ZT_{ave}} - 1}{\sqrt{1 + ZT_{ave}} + T_C/T_H}$$

where $T_{ave} = (T_H + T_C)/2$ is the average temperature of thermal gradient having a hot temperature ($T_H$) end and a cold temperature ($T_C$) end, and Z is a figure of merit, defined as $Z = S^2\sigma/\kappa$. The figure of merit Z depends on the macroscopic transport parameters of the materials, namely the Seebeck coefficient (S), electrical conductivity ($\sigma$), and thermal conductivity ($\kappa$). A large figure of merit is provided by a thermoelectric material having a large Seebeck coefficient, high electrical conductivity, and low thermal conductivity.

The Seebeck coefficient is further defined as the ratio of the open-circuit voltage to the temperature difference between the hot and cold junctions of a circuit exhibiting the Seebeck effect, or $S = V/(T_H - T_C)$. Since Z varies with temperature, a useful dimensionless figure of merit can be defined as ZT.

By the end of the 1950s, the best bulk thermoelectric materials were found to be alloys of bismuth telluride and antimony, which gave a room temperature ZT~1. Workers in the thermoelectric field have been attempting to improve the figure of merit over the past 40 years without much success. Increasing ZT is difficult because the three parameters S, $\sigma$, and k are all related to the free carrier concentration and are usually not independent. For example, doping typically increases the semiconductor's electrical conductivity, but decreases its Seebeck coefficient and increases the thermal conductivity. Efforts to reduce the lattice thermal conductivity by alloying also reduce the electrical conductivity by providing an extra scattering mechanism.

Dresselhaus and coworkers at MIT theoretically demonstrated that quantum confinement of electrons and phonons within nanowires of a thermoelectric material can increase the value of ZT. I-D nanowires in particular could reach ZT≈2-5 if the nanowire diameter lies in the range of 5-10 nanometers. Certain structures have been investigated, for example such as described in Heremans, J. P. et al., "Thermoelectric Power of Bismuth Nanocomposites"; Phys. Rev. Lett.; 2002, 88, 216801; Venkatasubramanian, R. et al., "Thin-film thermoelectric devices with high room temperature figures of merit"; Nature; 2001, 413, 597-602; Harman, T. C. et al., "Thermoelectric quantum dot superlattices with high ZT"; Electron. Mater.; 2000, 29, L1-L4; Rabin, O. et al., "Anomalously high thermoelectric figure of merit in $Bi_{1-x}Sb_x$ nanowires by carrier pocket alignment"; APL; 2001, 79, 81-83; and Dresselhaus, M. S. et al., "Low-dimensional thermoelectric materials"; PSS; 1999, 41, 679-682. However, these approaches do not provide a simple approach to making large-scale, low-cost thermoelectric devices. Conventional semiconductor device fabrication methods are unsuitable for manufacturing bulk samples, and are often expensive.

In automobiles, about 70 percent of energy derived from fuel is lost to waste heat and engine cooling. Only a small proportion of energy provided by fuel combustion is used, and a large amount of thermal energy is thrown away. Recovery of waste thermal energy is a big challenge in automotive industries due to the increasing energy crisis. Thermoelectric conversion of thermal energy to electrical energy could be an effective way to obtain electrical energy from otherwise wasted heat production. However, direct thermal to electric conversion (DTEC) technology currently faces two major challenges: low conversion efficiency and insufficient power density. Hence, improved materials and devices having high thermoelectric conversion efficiency are urgently required.

In response to the need for high thermoelectric conversion efficiency materials, Zhang et al. have investigated thermoelectric materials comprising two or more components, at least one of which is a thermoelectric material (U.S. Pat. App. No. 2006/0118158). However, a given thermoelectric material system can have a wide range of compositions that may, or may not, exhibit high ZT values. Therefore, a process to model, calculate and/or determine an optimum range of compositions in which a thermoelectric material exhibits high ZT values would be desirable.

SUMMARY OF THE INVENTION

A process for determining an optimum range of compositions for a nanocomposite thermoelectric material system, within which the material may exhibit generally high figure of merit values, is provided. The process is performed for a nanocomposite thermoelectric material system having a first component and a second component made from nanoparticles. The process includes selecting a plurality of material compositions for a nanocomposite thermoelectric material system to be investigated and calculating a thermal conductivity value and calculating an electrical resistance value for each material composition selected. In addition, at least one Seebeck coefficient is determined for the material compositions selected. Then, a plurality of figure of merit values are calculated using the calculated plurality of thermal conductivity values, the calculated plurality of electrical resistivity values and the determined at least one Seebeck coefficient. After the plurality of figure of merit values are calculated, an optimum compositional range can be determined within which the largest ZT values may be exhibited.

The plurality of thermal conductivity values can be calculated as a function of the scattering cross section of the second component nanoparticles and the scattering cross section can be a function of the interfacial surface area of between second component nanoparticles and the first component. The determination of the scattering cross section, the interfacial surface area, and thus the thermal conductivity, can take into account the size of the second component nanoparticles and/or the size distribution of the second component nanoparticles. In addition, an interfacial property of the second component nanoparticles can be considered when calculating the plurality of thermal conductivity values.

In some instances, the figure of merit values for the material system are calculated using the expression:

$$ZT = S^2 T/k\pi$$

Wherein ZT is the dimensionless figure of merit, S is the Seebeck coefficient, T is temperature in Kelvin, k is the thermal conductivity and $\rho$ is the electrical resistivity for a given material composition.

DETAILED DESCRIPTION OF THE INVENTION

The present invention discloses a process for determining an optimum range of compositions for a nanocomposite thermoelectric material system, within which the material system may exhibit generally high figure of merit values. As such, the process has utility for improving the efficiency of experimental design and production of thermoelectric materials.

The process for determining an optimum range of compositions for a nanocomposite thermoelectric material system considers a variety of relevant factors, parameters and the like in order to determine which material systems should be considered and/or which range of compositions should be studied in more detail. A thermoelectric material exhibiting a dimensionless high figure of merit (ZT) needs to possess a high Seebeck coefficient (S) for high voltage generation, a low electrical resistivity ($\rho$) to minimize Ohmic losses and a low thermal conductivity (k) to minimize heat conduction. Typically, these three parameters are interdependent with an increase of the Seebeck coefficient resulting in an increase in electrical resistivity, whereas a decrease in the electrical resistivity results in an increase of the thermal conductivity. At least one approach for obtaining high figure of merit values has investigated the insertion of nanoparticles within a thermoelectric material (U.S. Pat. App. No. 2006/0118158). Materials using this approach can result in phonons being scattered by the nanoparticles, thereby reducing the lattice thermal conductivity while leaving the electrical resistivity and Seebeck coefficient for the thermoelectric host matrix unchanged.

Elemental substitutions, also known as atomic substitutions, in potential thermoelectric materials have imperfections on the order of 1 angstrom (Å). Thus alloying additions can result in the scattering of short-wavelength phonons much more effectively than mid- and long-wavelength phonons. Therefore, mid- and long-wavelength phonons dominate the heat conduction in alloys and thermoelectric materials that have been doped with other elements not originally within the starting material. In the alternative, the inclusion of zero or additions such as nanoparticles in the size range of phonon wavelengths introduces another scattering mechanism that affects mid- and/or long-wavelength phonons, thereby providing an opportunity to reduce the thermal conductivity of such materials below the alloy limit. However, which nanoparticles with respect to their composition, size and size distribution, and which host matrix the nanoparticles should be added to has heretofore been a difficult task to predict.

In response to the difficulty in predicting successful thermoelectric material systems, a process to perform just this task has been developed. An embodiment of the process includes the modeling of lattice thermal conductivity for a nanocomposite wherein the thermal conductivity (k) is given by the Callaway formula shown in Equation 1:

$$k = \frac{k_B}{2\pi^2 v}\left(\frac{k_B T}{\hbar}\right)^3 \left(I_1 + \frac{I_2^2}{I_3}\right) \quad (1)$$

where $k_B$ is the bulk thermal conductivity, v is the speed of sound, h is Planck's constant and:

$$I_1 = \int_0^{\theta_n/T} \frac{\tau_e x^4 e^x}{(e^x - 1)^2} dx \quad (2)$$

$$I_2 = \int_0^{\theta_n/T} \frac{\tau_e x^4 e^x}{\tau_N (e^x - 1)^2} dx \quad (3)$$

$$I_3 = \int_0^{\theta_n/T} \left(1 - \frac{\tau_e}{\tau_N}\right) \frac{x^4 e^x}{\tau_N (e^x - 1)^2} dx \quad (4)$$

The relaxation time ($\tau$) is given by $$\tau_c^{-1} = \tau_B^{-1} + \tau_U^{-1} + \tau_n^{-1} \tau_A^{-1} + \tau_{e-ph}^{-1} + \tau_D^{-1} \quad (5)$$

where $\tau_c$ is the total relaxation time, $\tau_B$ is the relaxation time for boundary scattering, $\tau_U$ is the relaxation time for Umklapp phonon-phonon scattering, $\tau_N$ is the relaxation time for normal phonon-phonon scattering, $\tau_A$ is the relaxation time for lattice imperfections due to alloying, $\tau_{e-ph}$ is the relaxation time for electron-phonon scattering and $\tau_D$ is the time for lattice imperfections due to defects. The various relaxation times can be expressed as:

$$\tau_B^{-1} = \frac{v}{L_E} \quad (6)$$

$$\tau_N^{-1} = B_N \omega^2 T^3 \quad (7)$$

$$\tau_U^{-1} = B_U \omega^2 T^3 e^{-\frac{\theta_D}{nT}} \quad (8)$$

$$\tau_A^{-1} = A\omega^4 \tau_A^{-1} = A\omega^4 \quad (9)$$

$$\tau_D^{-1} = v \cdot \sigma_{scat}(\chi) \cdot \eta \quad (10)$$

and $$\tau_{e-ph} = \frac{E_d^2 m^{*3} v}{4\pi \hbar^4 d_m T^*} \ln\left(\frac{1+\exp(-T^* + \eta_F^* - x^2/16T^* + x/2)}{1+\exp(-T^* + \eta_F^* - x^2/16T^* - x/2)}\right) \quad (11)$$

where $L_E$ is a characteristic length perpendicular to the direction of heat flow, $B_N$ and $B_U$ and material property constants, $\omega$ is the circular frequency of the phonons, $\theta_D$ is the Debye temperature, n is a constant, A is an adjustable parameter, $\sigma_{scat}$ is the scattering cross section of the second component nanoparticles which is a function of $\chi$ a size parameter, and $\eta$ is the concentration. In addition, $E_d$ is the deformation potential, $m^*$ is the effective mass, $d_m$ the mass density, $T^*$ the reduced carrier energy at the speed of sound for electrons and $\eta^*_F$ the reduced chemical potential for electrons.

In the scattering cross section calculation, the nanoparticle size and size distribution are considered and can be calculated using Equation 12:

$$\sigma_{Scat} = \int_0^\infty \text{area} \cdot \text{scattering efficiency} \cdot \text{gammafunction} \, dR = \int_0^\infty \pi R^2 \left(\frac{\sigma_{total}}{\pi R^2}\right)\left(\frac{R^{A-1} e^{-\frac{R}{B}}}{B^A \Gamma(A)}\right) dR \quad (12)$$

where $$A = \frac{R_M^2}{SD^2} \quad (13)$$

$$B = \frac{SD^2}{R_M} \quad (14)$$

and $R_M$ is the mean radius of the nanoparticles and SD is the standard deviation of the mean radius of the nanoparticles. The total scattering cross section is represented by two extremes. One extreme is the Rayleigh scattering cross section and the other extreme is the near-geometrical cross section. The total scattering cross section can be expressed as a function of mass difference ($\Delta M/M$) and spring constant difference ($\Delta K/K$) between a nanoparticle and the host matrix.

The interfacial surface area is a measure of the interface between the host matrix and the second component nanoparticles which is also a measure of the scattering cross section for phonons. The interfacial surface area of the second component nanoparticles in the host matrix can be represented by:

$$A_I = N_P \int_0^\infty 4\pi r^2 g(r) dr \quad (15)$$

and the total volume of the nanoparticles by:

$$V_P = N_P \int_0^\infty \frac{4}{3}\pi r^3 g(r) dr \quad (16)$$

Thus total volume of the second component nanoparticles related to the total volume of the composite can be expressed as:

$$V_P = \Phi_P \quad (17)$$

and by combining Equations 15, 16 and 17 the expression for interfacial surface area per unit volume can be expressed as:

$$\frac{A_I}{V} = 3\phi_P \frac{\int_0^\infty r^2 g(r) dr}{\int_0^\infty r^3 g(r) dr} \quad (18)$$

The gamma distribution ($\phi_P$) can be determined by evaluating the integral in Equation 18 analytically and is given by the expression:

$$\frac{A_I}{V} = 3\phi_P \frac{R_M}{R_M^2 + 2SD^2} \quad (19)$$

Figure 1:
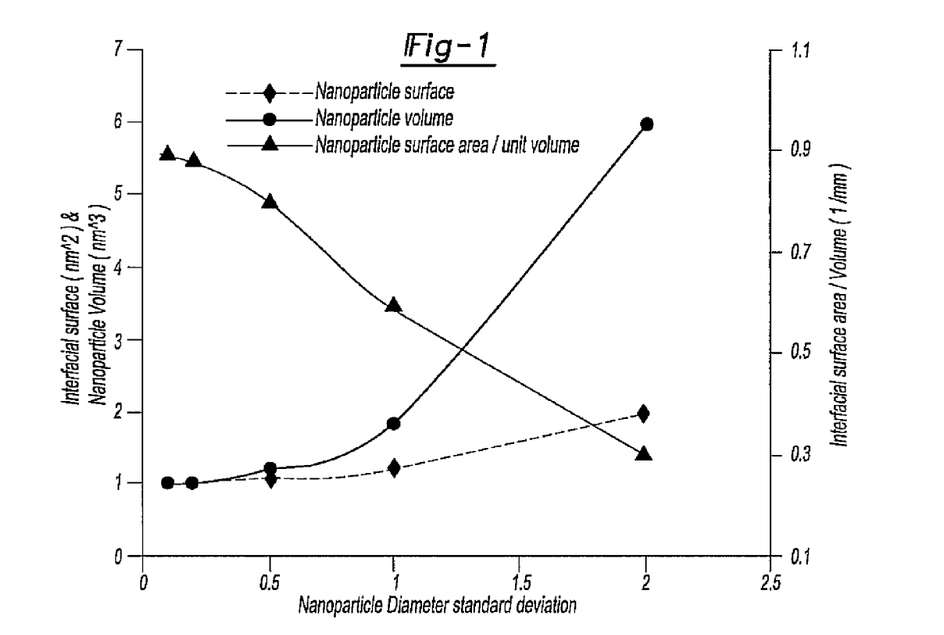
FIG. 1 is a graphical plot illustrating nanoparticle interfacial surface area, volume and interfacial surface area per unit volume as function of standard deviation for nanoparticle diameter.

It is of interest to note that the interfacial surface area per unit volume can actually decrease with an increasing standard deviation of the second component nanoparticle size. For example, FIG. 1 illustrates a plot of the nanoparticle surface area and the nanoparticle volume as a function of an increasing nanoparticle size standard deviation. As shown in this figure, the nanoparticle volume increases at a faster rate than the nanoparticle surface area. The ratio of the nanoparticle surface area to the nanoparticle volume determines the interfacial surface area per unit volume according to Equation 18. As a result, the interfacial surface area per unit volume actually decreases as the nanoparticle size distribution increases.

A mean free path for a phonon can also be an important parameter for understanding and/or modeling an optimum range of compositions for a nanocomposite thermoelectric material system. The mean free path, for the purposes of the present invention, is defined as the average distance traveled by a phonon before being scattered by an obstacle. Such obstacles can be by a boundary, a defect, another phonon and/or nanoparticle inclusions. The total mean free path can be expressed as:

$$L = v\tau \quad (20)$$

where L is the total mean free path, v is the phonon velocity which is equal to the acoustic velocity, and $\tau$ is the relaxation time provided by Equations 6-10. Similar to the relaxation time given by Equation 5, the total mean free path due to different scattering processes can be expressed by:

$$L^{-1} = L^{-1}_B + L^{-1}_A + L^{-1}_U + L^{-1}_D \quad (21)$$

Using Equations 6-10 and 20, the expressions for the mean free paths for different scattering processes can be determined by:

$$L_B = L_E \qquad (22)$$

$$L_A = \frac{v}{A\omega^4} \qquad (23)$$

$$L_N = \frac{v}{B_N \omega^2 T^3} \qquad (24)$$

$$L_U = \frac{v}{B_N \omega^2 T e^{-\frac{\theta_D}{nT}}} \qquad (25)$$

$$L_D = \frac{1}{\sigma_{Scat}(\chi)\eta} \qquad (26)$$

Figure 2:
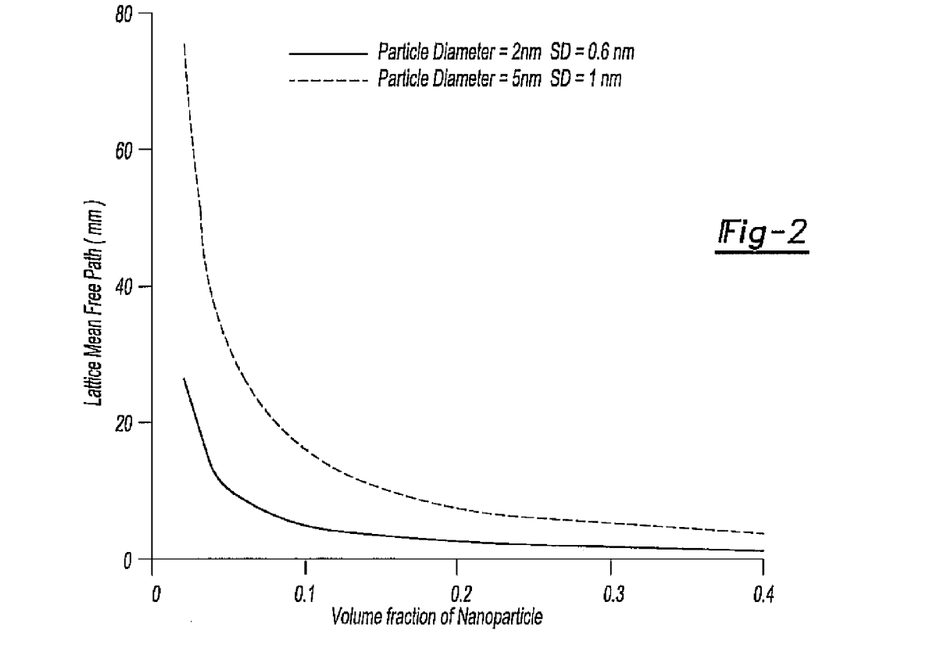
FIG. 2 is a graphical plot illustrating lattice mean free path as a function of volume fraction of nanoparticles.

The number density due to particle size distribution for the nanoparticles can be given by:

$$\eta = \frac{\text{Volume fraction of nanoparticles } (\phi_P)}{\int_0^\infty \frac{4}{3}\pi R^3 \left(\frac{R^{A-1} e^{-\frac{R}{B}}}{B^A \Gamma(A)}\right) dR} \qquad (27)$$

thereby allowing the effect of nanoparticle volume percentage on lattice mean free path ($L_D$) to be shown. For example, FIG. 2 illustrates the effect of nanoparticle volume percentage on lattice mean free path due to nanoparticle sizes of 2 nanometers and 5 nanometers. As expected, the scattering of phonon increases as the quantity of nanoparticles are included into the host matrix. It is of interest to note that at relatively low concentrations monodispersed nanoparticles having a mean diameter of 2 nanometers results in a material having a mean free path of less than 20 nanometers, while nanoparticles having a mean diameter of 5 nanometers results in a mean free path of greater than 70 nanometers. In addition, material having nanoparticles with mean diameters of 5 nanometers will exhibit a lattice mean free path greater material having 2 nanometer particles, even at higher nanoparticle volume fractions.

Figure 3:
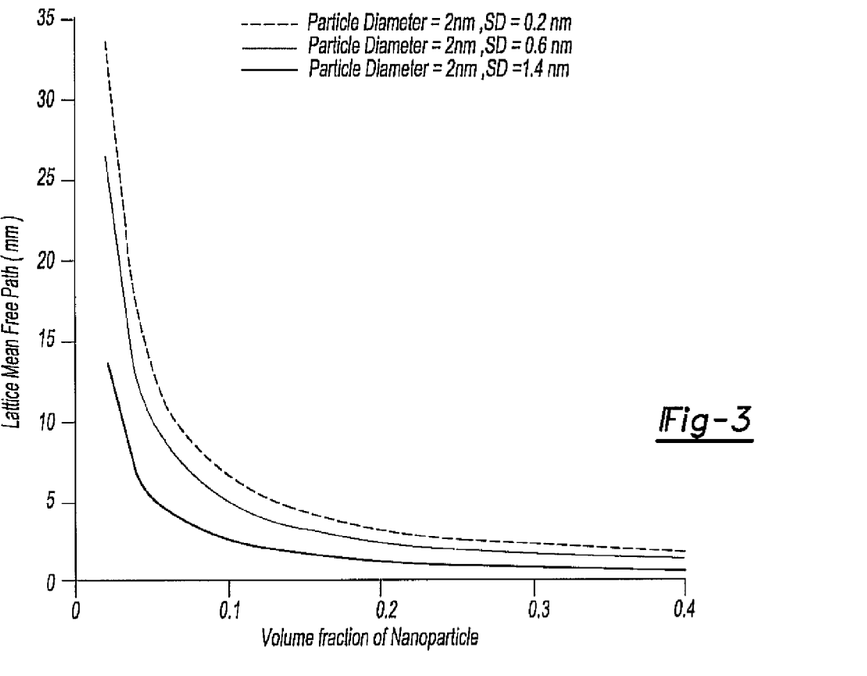
FIG. 3 is a graphical plot illustrating lattice mean free path as a function of volume fraction of nanoparticles.

Turning to FIG. 3, the effect of size distribution on lattice mean free is shown for a nanocomposite material having nanoparticles with a mean diameter of 2. Of particular interest is the result that an increase in the standard deviation of the nanoparticle mean diameter results in a decrease in the lattice mean free path.

An analytical expression for mean interparticle distance can be described as:

$$<a> = \left[\frac{4\pi}{3\phi_P R_M}(R_M^2 + SD^2)(R_M^2 + 2SD^2)\right]^{1/3} \qquad (31)$$

which aids in describing that a wide range of size distribution for the mean diameter of the nanoparticles results in a decrease of the mean free path even, though the interparticle distance increases. Not being bound by theory, the inventors propose that a wide range of distribution of nanoparticle size results in scattering of a wide range of phonon wavelengths which in fact overtakes the effect of an increasing mean interparticle distance.

Figure 4:
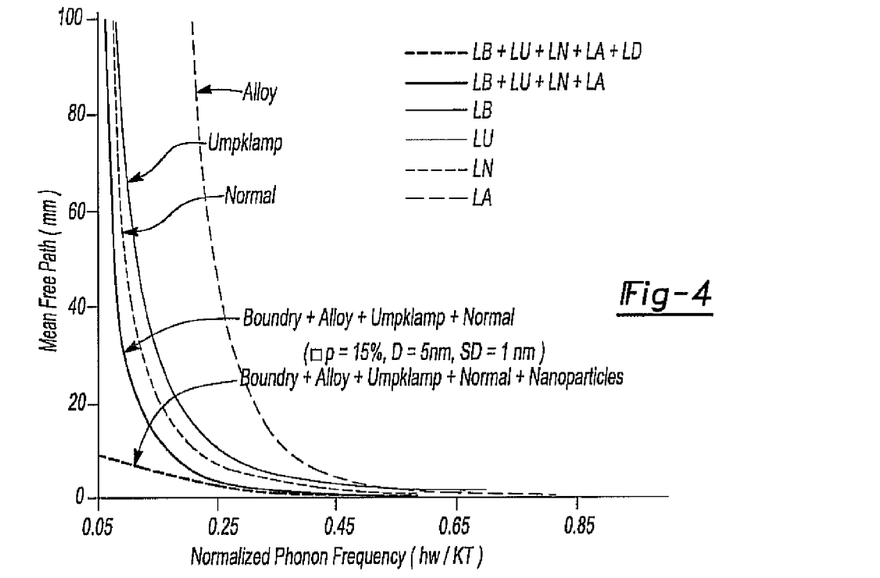
FIG. 4 is a graphical plot illustrating mean free path as a function of normalized phonon frequency.

Returning to Equation 24, the total scattering due to the different scattering processes can be plotted in terms of a normalized phonon frequency ($\hbar\omega/k_B T$) as illustrated in FIG. 4. As illustrated in this figure, low frequency phonons (that is long wavelength phonons) are not affected by small atomic imperfections and thus produce large mean free path values due to alloy scattering. In addition, when scattering due to boundary+alloy+Umpklamp+normal processes is compared to boundary+alloy+Umpklamp+normal+nanoparticles scattering processes, it is evident that the addition of nanoparticles significantly reduces the mean free path for low and mid-frequency phonons to below 10 nanometers.

The Seebeck coefficient can be estimated as a function of the concentration of the second component nanoparticles, or in the alternative the Seebeck coefficient can be assumed to be the same as for the host matrix, so long as the host matrix forms a continuous network throughout the material. This is a particularly reasonable approximation in the case of second component nanoparticles in the form of insulating materials such as titanium dioxide ($TiO_2$) and silica ($SiO_2$). In contrast, it is known that the addition of second component nanoparticles that are insulating in nature reduces the electrical conductivity of the nanocomposite material. The approximation of the electrical resistivity of such a material can be estimated using effective medium approximation (EMA) for a binary alloy. In addition, Maxwell's formula can be used to determine the effective electrical resistivity (or conductivity) of a two phased disordered composite medium. For an arbitrary dimensionality of d, the Maxwell formula and the EMA expressions in terms of conductivities $\sigma_1$ and $\sigma_2$, and volume fractions $\phi_1$ and $\phi_2$ can be expressed as:

$$\frac{\sigma_e - \sigma_1}{\sigma_e - (d-1)\sigma_1} = \phi_2 \frac{\sigma_2 - \sigma_1}{\sigma_2 - (d-1)\sigma_1} \qquad (32)$$

$$\phi_1 \frac{\sigma_1 - \sigma_e}{\sigma_1 - (d-1)\sigma_e} = \phi_2 \frac{\sigma_2 - \sigma_e}{\sigma_2 - (d-1)\sigma_e} \qquad (33)$$

$$\sigma_e = \frac{1}{4}\{(3\phi_2 - 1)\sigma_2 + (3\phi_1 - 1)\sigma_1 + \qquad (34)$$
$$[((3\phi_2 - 1)\sigma_2 + (3\phi_1 - 1)\sigma_1)^2 + 8\sigma_1\sigma_2]^{1/2}\}$$

Thus, it is appreciated that once the Seebeck coefficient has been determined and the thermal conductivity and electrical resistivity have been calculated as a function of a range of compositions for a thermoelectric material system that the figure of merit can be calculated for each composition. In addition, a comparison of the figure of merit values as a function of the second component nanoparticle concentration affords for a range of compositions to be determined within which the figure of merit values are relatively high compared to other compositions within the nanocomposite thermoelectric material system.

In an effort to better illustrate the process for determining an optimum range of compositions for a nanocomposite thermoelectric material, and in no way limiting said process, an example of the process follows.

EXAMPLE

The efficiency of a thermoelectric generator depends on the figure of merit (ZT) and the ratio of high and low temperature base of the thermoelectric material. A good thermoelectric material is known to be one that can maintain a high ZT over a large temperature range. The process described above was used to study a p-type lead-tellurium (PbTe) matrix host having a bulk ZT equal to 0.5 at 473 Kelvin (K). The PbTe can be made from nanoparticles, or in the alternative not be made from nanoparticles. Second component nanoparticles of $TiO_2$ were used for demonstration of the process. Referring back to Equations 1-11, the constants shown in Table 1 were used for calculations. Using these constants, the relaxation time given in Equation 5 and required in Equations 2-4 was calculated wherein the scattering cross section due to nanoparticles of Equation 12 was determined as a function of the quantity of second component $TiO_2$ nanoparticles within the PbTe host matrix, the mean diameter of the $TiO_2$ nanoparticles and/or the size distribution of the $TiO_2$ nanoparticles.

TABLE 1

| Bulk PbTe | Electron-Phonon Scattering |
| --- | --- |
| $\theta_D = 126$ K | $h = 1.054 \times 10^{-34}$ J·s |
| $B_u = 6.2 \times 10^{-18}$ s/K | $k_B = 1.38 \times 10^{-23}$ m² kg s$^{-2}$ K$^{-1}$ |
| n = 4.2 | $E_d = 16 \times 10^{-19}$ J |
| $A = 4 \times 10^{-42}$ s³ | m* = 0.01 × 9.109 × 10$^{-31}$ kg |
| v = 1730 m/s | $\delta_m = 334.8 \times 10^{-4}/(6.023 \times 0.6462^3)$ kg/m³ |
| $L_E = 3.5 \times 10^{-5}$ m | $\eta^*_F = 0.1 \times 1.6 \times 10^{-19}$ J |
| $B_N = 9.0 \times 10^{-23}$ s/K³ | |

Figure 5:
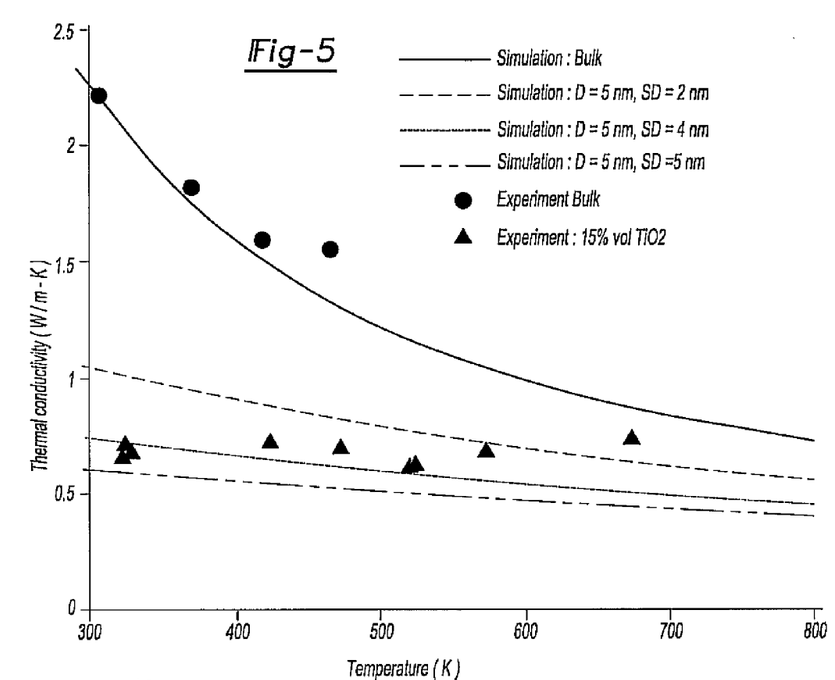
FIG. 5 is a graphical plot illustrating a comparison between experimental data and simulated data for thermal conductivity as a function of temperature.

Turning to FIG. 5, a simulation or calculation of the thermal conductivity of bulk PbTe and $TiO_2$ embedded PbTe for temperatures between 300-800° K. is shown. In addition, experimental data for bulk PbTe and 15 volume percent $TiO_2$ embedded PbTe is shown for comparison. Based on the comparison between the simulation results and the experimental data, it is clear that generally good agreement between the two is obtained.

Figure 6:
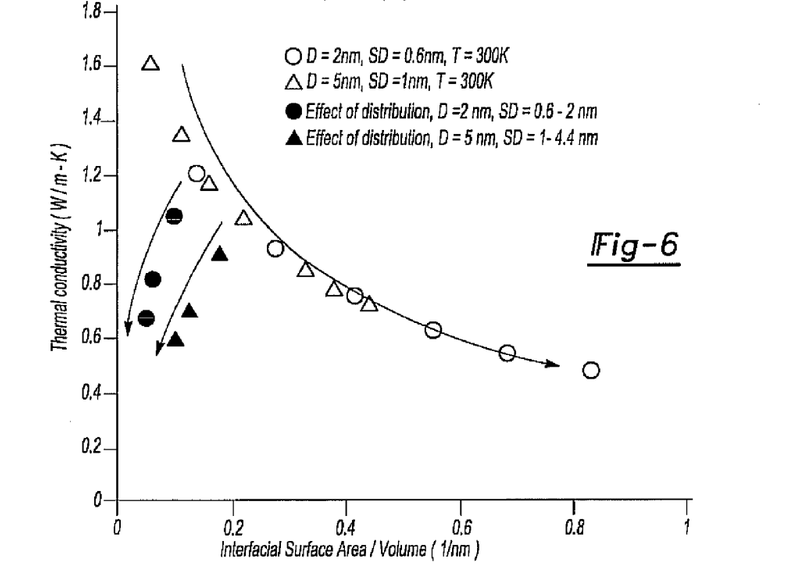
FIG. 6 is a graphical plot illustrating thermal conductivity as a function of interfacial surface area per unit volume.

Regarding the interfacial surface area per unit volume, the calculation of the thermal conductivity for a PbTe host matrix with $TiO_2$ nanoparticle concentrations ranging from 5 to 40 volume percent is shown in FIG. 6 for two nanoparticle sizes, a temperature of 300° K. and various size distributions. As shown in this figure by the solid line tracking the open circle and open triangle data symbols, an increase in interfacial surface area results in a decrease in thermal conductivity. However, what may not be appreciated is the fact that the thermal conductivity for a given mean diameter decreases with an increase in size distribution, even though the interfacial surface area per unit volume decreases. For example, the closed circle and closed triangle data symbols represent the thermal conductivity data for PbTe—$TiO_2$ nanocomposites having a mean $TiO_2$ nanoparticle diameter of 2 and 5 nanometers, respectively, with a standard deviation that varies from 0.6 to 2 nanometers for the 2 nanometer particles and 1 to 4.4 nanometers for the 5 nanometer particles. It is evident that when the standard deviation is moderate—such as the 0.6 nanometer standard deviation for the 2 nanometer $TiO_2$ particles as represented by the open circle data symbols and the 1.0 nanometer standard deviation for the 5 nanometer particles as represented by the open triangle data symbols—the thermal conductivity for both the 2 and 5 nanometer size nanoparticles follow the same universal plot. However, increasing the $TiO_2$ nanoparticle standard deviation incrementally from 0.6 to 2 nanometers for the 2 nanometer particles and 1 to 4.4 nanometers for 5 nanometer particles results in a decrease in the thermal conductivity as shown by the solid circle and solid triangle data symbols, despite the fact that the interracial surface area decreases. Thus from this figure, it is clear that a decrease in the thermal conductivity of a nanocomposite thermoelectric material can be obtained without necessarily having to increase the quantity of second component nanoparticles.

Figure 7:
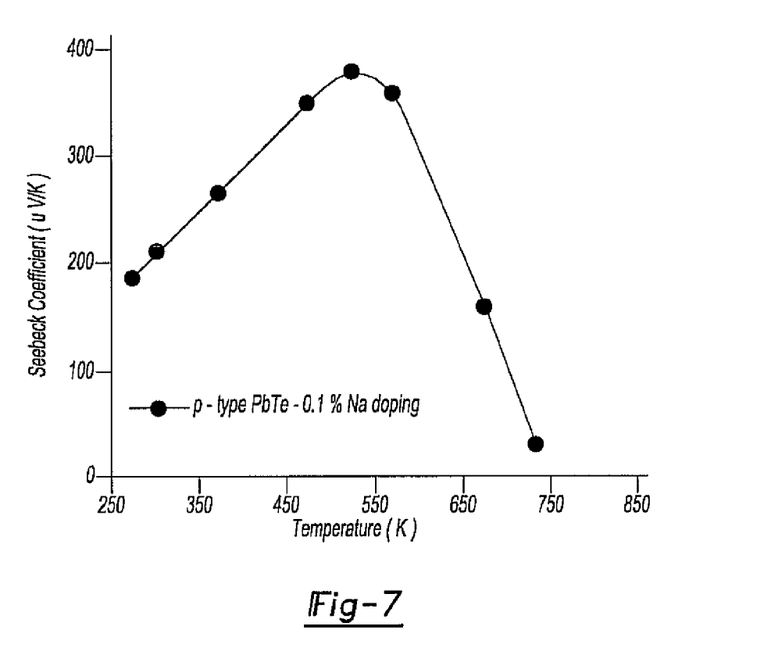
FIG. 7 is a graphical plot illustrating Seebeck coefficient as a function of temperature for p-type PbTe.
Figure 8:
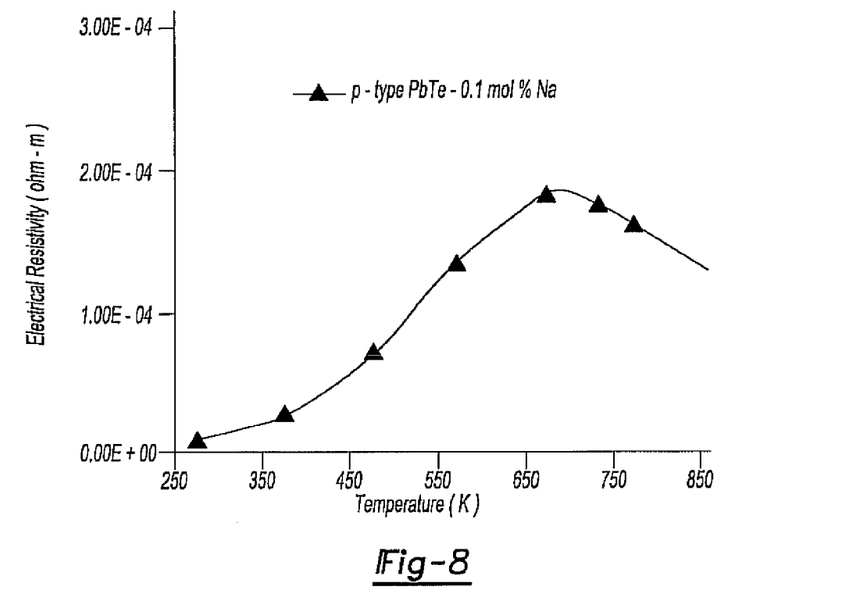
FIG. 8 is a graphical plot illustrating electrical resistivity as a function of temperature for p-type PbTe.
Figure 9:
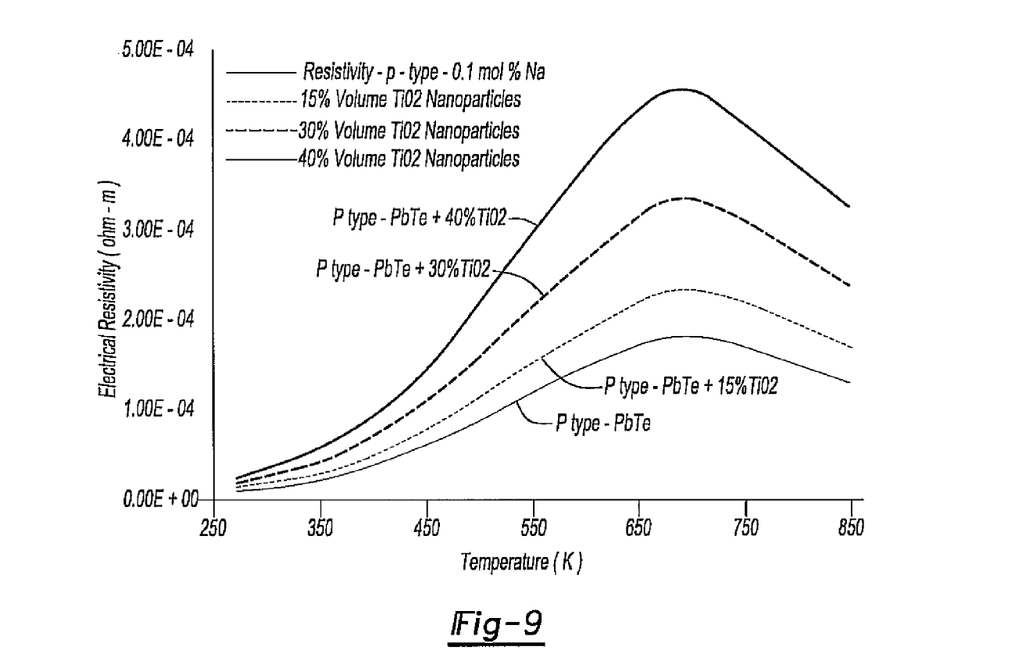
FIG. 9 is a graphical plot illustrating electrical resistivity as a function of temperature for the PbTe—TiO$_2$ nanocomposite material system.

Turning now to determining the Seebeck coefficient and electrical resistivity of the PbTe—$TiO_2$ thermoelectric material system, FIG. 7 illustrates experimental values of the Seebeck coefficient for a p-type PbTe thermoelectric host matrix. These values were used and assumed since the PbTe—$TiO_2$ thermoelectric material system for this study was assumed to have a continuous network of the host PbTe thermoelectric material. Regarding the electrical resistivity values for the PbTe—$TiO_2$ thermoelectric material system, the data shown in FIG. 8 was used with Equations 32-34 to calculate the electrical resistivity values as a function of volume percent $TiO_2$ nanoparticles. These values are shown in FIG. 9.

In bulk p-type PbTe, the electronic contribution to thermal conductivity is small compared to the lattice thermal conductivity. However, the addition of $TiO_2$ nanoparticles within the host matrix can reduce the lattice thermal conductivity to such an extent that the electronic contribution cannot be ignored. Therefore, it can be important to consider thermal conduction due to electrons. The electronic thermal conductivity ($k_e$) can be related to electrical conductivity ($\sigma_e$) by the expression:

$$\frac{k_e}{\sigma_e} = LT \tag{35}$$

where L is the Lorentz number and T is the temperature. For a system like p-type PbTe, the Lorentz number can be estimated as $2.4 \times 10^{-8}$ W-ohm/K². Using electrical resistivity data obtained from the literature, the electronic contribution to the overall thermal conductivity can be estimated. In addition, the increase in electrical resistivity due to the addition of $TiO_2$ nanoparticles can be determined if so desired.

Figure 10:
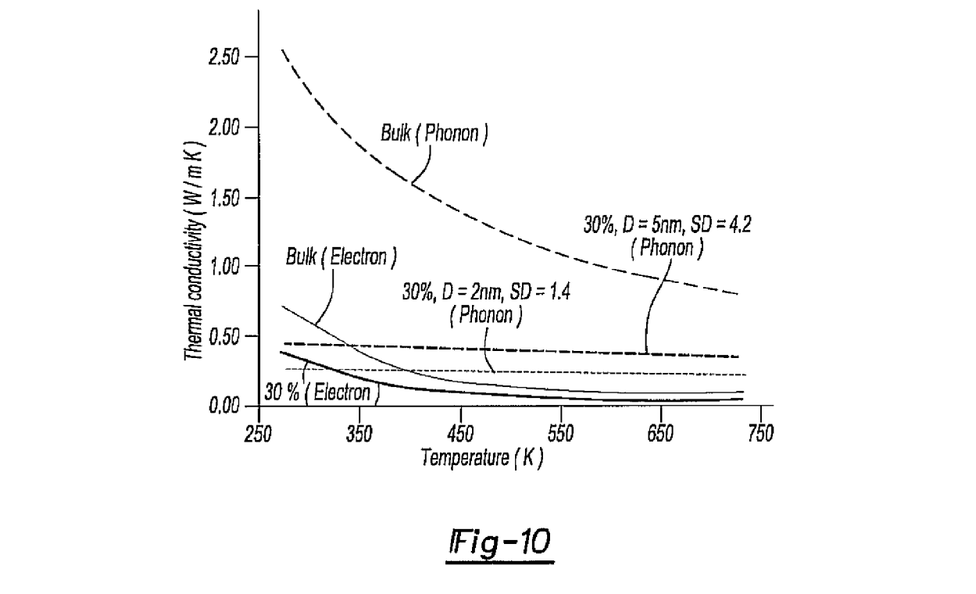
FIG. 10 is a graphical plot illustrating thermal conductivity as a function of temperature for the PbTe—TiO$_2$ nanocomposite material system.
Figure 11:
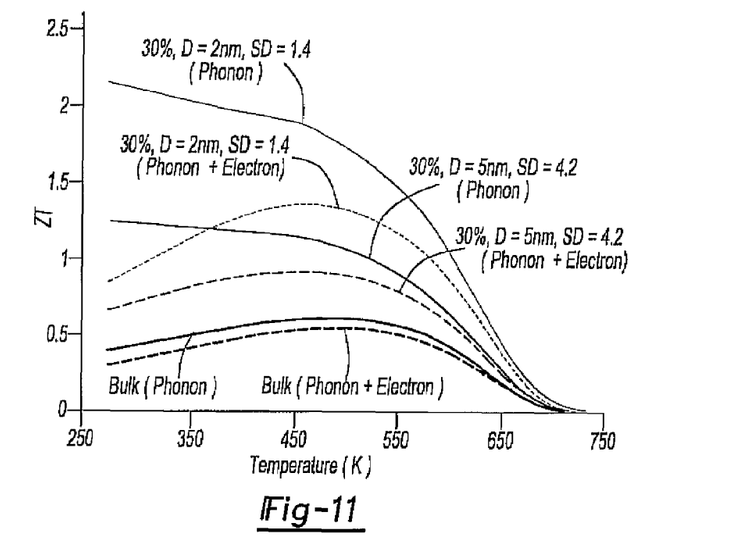
FIG. 11 is a graphical plot illustrating figure of merit as a function of temperature for the PbTe—TiO$_2$ nanocomposite material system.

FIG. 10 illustrates a comparison of the electronic and phonon thermal conductivity for bulk PbTe material and for a PbTe—$TiO_7$ nanoparticle system containing 30 volume percent of $TiO_2$. In addition, a comparison of figure of merit values calculated as a function of phonon contribution and phonon+electron contribution is shown in FIG. 11. From FIGS. 10 and 11, it is clear that the electronic thermal conductivity is comparable to the phonon thermal conductivity in PbTe—$TiO_2$ nanocomposite materials. This is also reflected in the estimation of the figure of merit.

Figure 12:
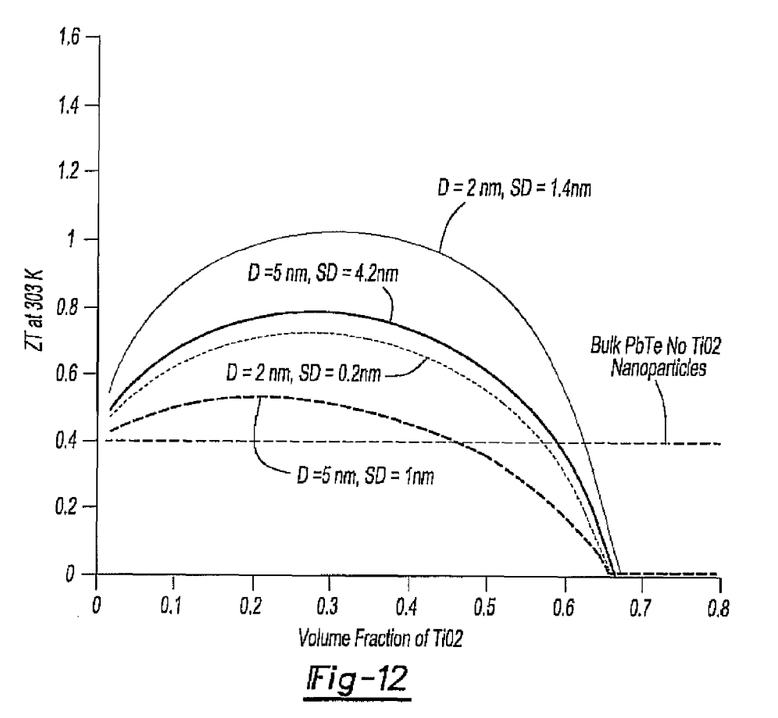
FIG. 12 is a graphical plot illustrating figure of merit as a function volume fraction of TiO$_2$ for the PbTe—TiO$_2$ nanocomposite material system at 303 K.
Figure 13:
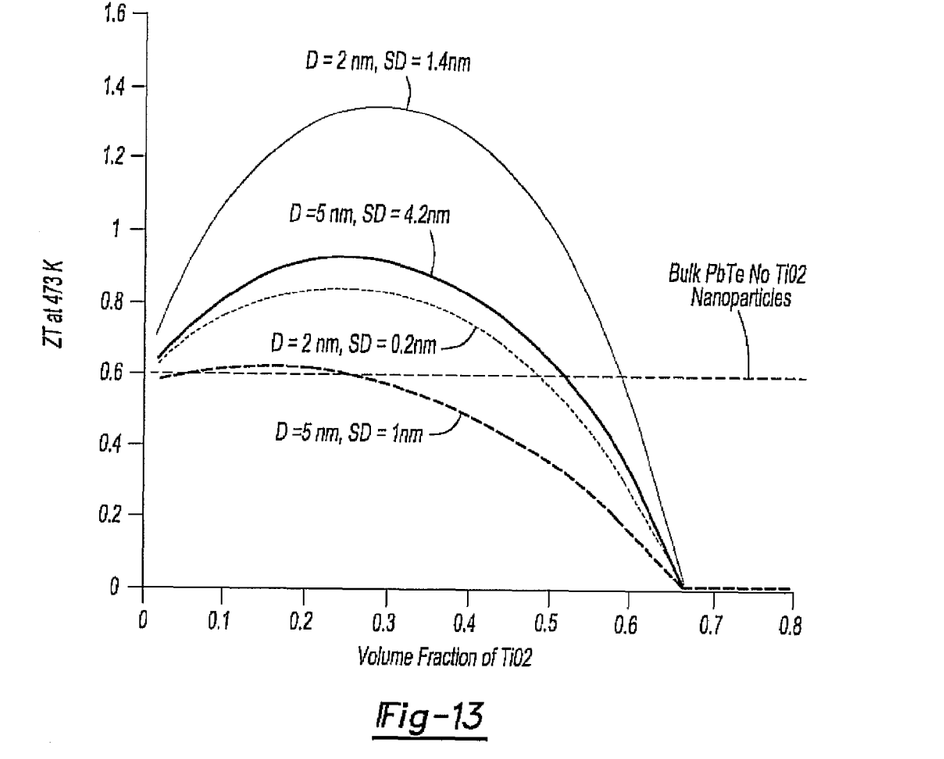
FIG. 13 is a graphical plot illustrating figure of merit as a function volume fraction of TiO$_2$ for the PbTe—TiO$_2$ nanocomposite material system at 473 K.

Having determined the effect of electrons and phonons to the overall thermal conductivity, the figure of merit can be plotted against the volume percentage of $TiO_2$ for different mean diameters and different size distributions of $TiO_2$ nanoparticles. These results are shown in FIG. 12 for a temperature of 303 K and FIG. 14 for a temperature of 473 K. Both FIGS. 12 and 13 illustrate a bell-shaped curve wherein an optimum range of compositions for the PbTe—$TiO_2$ nanocomposite thermoelectric material exhibits generally high figure of merit values. As shown in FIG. 12, a PbTe host matrix with between 0.2 and 0.4 volume fraction of $TiO_2$ nanoparticles having a mean diameter of 2 nanometers with a standard deviation of 1.4 nanometers exhibits high ZT values. As such, this graph, and thus the process, provides valuable information as to which compositions should be studied in greater detail. Likewise, FIG. 13 shows a range of ZT values for the PbTe—$TiO_2$ system wherein a volume fraction of $TiO_2$ between 0.2 and 0.4 provides the highest ZT values for most mean diameter particle sizes and standard deviations.

It is appreciated that the process of calculating the thermal conductivity and electrical resistivity for a given nanocomposite material system as a function of material compositions affords for the calculation of figure of merit values as a function of the compositions. In this manner, researchers can estimate which matrix host-nanoparticle systems are more likely to exhibit relatively high ZT values and/or which compositions or range of compositions within a particular system may provide the highest ZT values. This range of compositions with the associated high ZT values can also be compared with other material properties such as mechanical property data, chemical property data and the like, in order to choose an optimum thermoelectric material composition for a given application. As such, the process provides a valuable tool to guide experimental design of thermoelectric materials.

As disclosed above, the plurality of material positions to be investigated can include a first component with a volume fraction of a second component ranging from 0.0 to 1.0. In some instances, the material compositions to be investigated can include the first component with a volume fraction of the second component ranging from 0.0 to 0.7. The plurality of thermal conductivity values are calculated as a function of the scattering cross section of the second component nanoparticles for the plurality of material compositions being investigated. In addition, the scattering cross section can be a function of the interfacial surface area of the second component nanoparticles for the plurality of material compositions being investigated. The function of the plurality of material compositions being investigated can include the size of the second component nanoparticles, the size distribution of the second component nanoparticles and an interfacial property of the second component nanoparticles. In some instances, an interfacial interaction property between the second component nanoparticles and the first component can be used.

It is appreciated that the thermoelectric device can be designed and developed using the process disclosed herein, the thermoelectric device having a first electrical contact, a second electrical contact, and a thermoelectric bulk material located within an electrical path between the first electrical contact and the second electrical contact. The thermoelectric bulk material can include a first powdered component having a particulate form, the first powdered component being electrically conducting, and a second powdered component having a particulate form, the second powdered component having an electrical conductivity substantially less than the first powdered component. The first and second powdered components can retain the particulate form in the bulk thermoelectric material and the thermoelectric bulk material can be a composite that has nanostructures of the first powdered component. The first component can be a metal or a semiconductor. The second component can be an electrical insulator in the form of a ceramic. It is appreciated that the process can also be used for semiconductor-metal and semiconductor-semiconductor thermoelectric material systems.

The invention is not restricted to the illustrative examples described above. The examples are not intended as limitations on the scope of the invention. Methods, apparatus, compositions and the like described herein are exemplary and not intended as limitations on the scope of the invention. Changes therein and other uses will occur to those skilled in the art. The scope of the invention is defined by the scope of the claims.

We claim:

1. A process for manufacturing a nanocomposite thermoelectric material exhibiting a generally high figure of merit value, the nanocomposite thermoelectric material having a first component made from nanoparticles and a second component made from nanoparticles, the process comprising:

determining a plurality of material compositions to be investigated for the nanocomposite thermoelectric material;

calculating a plurality of thermal conductivity values as a function of scattering cross section of the second component nanoparticles for the material as a function of the plurality of material compositions to be investigated;

calculating a plurality of electrical resistivity values for the material as a function of the plurality of material compositions to be investigated;

determining at least one Seebeck coefficient for the material as a function of the plurality of material compositions to be investigated;

calculating a plurality of figure of merit values for the material as a function of the calculated plurality of thermal conductivity values, the calculated plurality of electrical resistivity values and the determined at least one Seebeck coefficient; and determining a generally maximum range of the figure of merit values for the material as a function of the plurality of material compositions to be investigated;

providing a plurality of the first component nanoparticles and a plurality of the second component nanoparticles; and combining a first quantity of the first component nanoparticles and a second quantity of the second component nanoparticles to form the nanocomposite thermoelectric material having a material composition within the plurality of material compositions corresponding to the generally maximum range of figure of merits values.

2. The process of claim 1, wherein the plurality of material compositions to be investigated includes the first component with a volume fraction of the second component ranging from 0.0 to 1.0.

3. The process of claim 1, wherein the scattering cross section is a function of the interfacial surface area of the second component nanoparticles for the plurality of material compositions to be investigated.

4. The process of claim 1, wherein the function of the plurality of material compositions to be investigated includes the size of the second component nanoparticles.

5. The process of claim 1, wherein the function of the plurality of material compositions to be investigated includes the size distribution of the second component nanoparticles.

6. The process of claim 1, wherein the function of the plurality of material compositions to be investigated includes an interfacial property of the second component nanoparticles.

7. The process of claim 1, wherein the function of the plurality of material compositions to be investigated includes an interfacial interaction property between the second component nanoparticles and the first component nanoparticles.

8. A process for manufacturing a nanocomposite thermoelectric material having a first component made from nanoparticles and a second component made from nanoparticles, the process comprising:

determining a plurality of material compositions to be investigated for the nanocomposite thermoelectric material having the first component made from nanoparticles and the second component made from nanoparticles;

calculating a plurality of thermal conductivity values as a function of scattering cross section of the second component nanoparticles for the material as a function of the plurality of material compositions to be investigated;

calculating a plurality of electrical resistivity values for the material as a function of the plurality of material compositions to be investigated;

determining at least one Seebeck coefficient for the material as a function of the plurality of material compositions to be investigated;

calculating a plurality of figure of merit values for the material using the expression:

$$ZT_i = S_i^2 ZT/k_i \rho_i$$

where $ZT_i$ represents the figure of merit for the plurality of material compositions to be investigated, $S_i$ represents the at least one Seebeck coefficient for the plurality of material compositions to be investigated, T represents a temperature being investigated in degrees Kelvin, $k_i$ represents thermal conductivity for the plurality of material compositions to be investigated and $\rho_i$ represents electrical resistivity for each of the plurality of material compositions to be investigated;

determining a generally maximum range of the figure of merit values for the material as a function of the plurality of material compositions to be investigated;

providing a plurality of the first component nanoparticles and a plurality of the second component nanoparticles; and combining a first quantity of the first component nanoparticles and a second quantity of the second component nanoparticles to form the nanocomposite thermoelectric material having a material composition within the plurality of material compositions corresponding to the generally maximum range of figure of merits values.

9. The process of claim 8, wherein the plurality of material compositions to be investigated includes the first component with a volume fraction of the second component ranging from 0.0 to 1.0.

10. The process of claim 8, wherein the scattering cross section is a function of the interfacial surface area of the second component nanoparticles for the plurality of material compositions to be investigated.

11. The process of claim 8, wherein the function of the plurality of material compositions to be investigated includes the size of the second component nanoparticles.

12. The process of claim 8, wherein the function of the plurality of material compositions to be investigated includes the size distribution of the second component nanoparticles.

13. The process of claim 8, wherein the function of the plurality of material compositions to be investigated includes an interfacial property of the second component nanoparticles.

14. The process of claim 8, wherein the function of the plurality of material compositions to be investigated includes an interfacial interaction property between the second component nanoparticles and the first component nanoparticles.

* * * * *

UNITED STATES PATENT AND TRADEMARK OFFICE
CERTIFICATE OF CORRECTION

PATENT NO. : 7,734,428 B2  Page 1 of 1
APPLICATION NO. : 11/875266
DATED : June 8, 2010
INVENTOR(S) : Debasish Banerjee et al.

It is certified that error appears in the above-identified patent and that said Letters Patent is hereby corrected as shown below:

Column 9, line 59 replace "interracial" with --interfacial--

Signed and Sealed this

Twenty-third Day of November, 2010

David J. Kappos
*Director of the United States Patent and Trademark Office*